US010531896B2

(12) United States Patent
Mannanal

(10) Patent No.: US 10,531,896 B2
(45) Date of Patent: Jan. 14, 2020

(54) DISTRACTION TUBE WITH WIRE CLAMP

(71) Applicant: Stryker European Holdings I, LLC, Kalamazoo, MI (US)

(72) Inventor: Subash K. Mannanal, Ramsey, NJ (US)

(73) Assignee: Stryker European Holdings I, LLC, Kalamazoo, MI (US)

(*) Notice: Subject to any disclaimer, the term of this patent is extended or adjusted under 35 U.S.C. 154(b) by 141 days.

(21) Appl. No.: 14/997,038

(22) Filed: Jan. 15, 2016

(65) Prior Publication Data
US 2017/0042579 A1 Feb. 16, 2017

Related U.S. Application Data

(60) Provisional application No. 62/203,174, filed on Aug. 10, 2015.

(51) Int. Cl.
*A61B 17/64* (2006.01)
*A61B 17/00* (2006.01)

(52) U.S. Cl.
CPC ...... *A61B 17/6466* (2013.01); *A61B 17/6416* (2013.01); *A61B 2017/00991* (2013.01)

(58) Field of Classification Search
CPC ........ A61B 17/6416; A61B 2017/6491; A61B 17/6466–6483
USPC .......................................................... 606/59
See application file for complete search history.

(56) References Cited

U.S. PATENT DOCUMENTS

| 1,201,864 | A |   | 10/1916 | Overmeyer |              |
|-----------|---|---|---------|-----------|--------------|
| 2,251,209 | A |   | 7/1941  | Stader    |              |
| 2,406,987 | A | * | 9/1946  | Anderson  | A61B 17/6441 |
|           |   |   |         |           | 606/59       |

(Continued)

FOREIGN PATENT DOCUMENTS

| EP | 0240034 A1 | 10/1987 |
|----|------------|---------|
| EP | 0314021 A2 | 5/1989  |

(Continued)

OTHER PUBLICATIONS

D.N.E., Inc., Pins Anywhere? S.E.A.L. Multi-Plane Mini by D.N.E., undated.

(Continued)

*Primary Examiner* — Jacqueline T Johanas
(74) *Attorney, Agent, or Firm* — Lerner, David, Littenberg, Krumholz & Mentlik, LLP

(57) ABSTRACT

Described herein are external fixation systems for correcting bone deformities in adjacent bones or fragments thereof. The systems herein include first and second elongate tubes that translate with respect to one another via rotation of an actuation member at an end of one of the rods. At least one housing member is coupled along a length of one of the tubes. The housing member includes at least clamping portion for clamping a portion of a fixation pin therein. When the housing member is in an unlocked state, the clamping portions can move in a variety of directions. When in a locked state, the housing member cannot move with respect to the tube that it is coupled to. The position and orientation of the fixation pin is also set. The locked and unlocked state of the housing member is determined by the positioning of a locking pin coupled to the housing member.

19 Claims, 8 Drawing Sheets

(56) References Cited

U.S. PATENT DOCUMENTS

| | | | |
|---|---|---|---|
| 2,497,626 A | 2/1950 | Persall | |
| 4,456,004 A | 6/1984 | Kenny | |
| 4,483,334 A * | 11/1984 | Murray | A61B 17/60 403/391 |
| 4,502,473 A | 3/1985 | Harris et al. | |
| 4,548,199 A | 10/1985 | Agee | |
| 4,570,625 A | 2/1986 | Harris et al. | |
| 4,600,000 A | 7/1986 | Edwards | |
| 4,611,586 A | 9/1986 | Agee et al. | |
| 4,628,919 A | 12/1986 | Clyburn | |
| 4,714,076 A | 12/1987 | Comte et al. | |
| 4,730,608 A | 3/1988 | Schlein | |
| 4,890,631 A * | 1/1990 | Hardy | A61B 17/62 606/59 |
| 4,895,141 A | 1/1990 | Koeneman et al. | |
| 4,968,316 A | 11/1990 | Hergenroeder | |
| 4,988,349 A | 1/1991 | Pennig | |
| 4,998,935 A | 3/1991 | Pennig | |
| 5,122,140 A | 6/1992 | Asche et al. | |
| 5,207,676 A | 5/1993 | Canadell et al. | |
| 5,281,221 A | 1/1994 | Tadych | |
| 5,393,161 A | 2/1995 | Mata et al. | |
| RE34,985 E | 6/1995 | Pennig | |
| 5,429,637 A | 7/1995 | Hardy | |
| 5,437,666 A | 8/1995 | Tepic et al. | |
| 5,545,162 A | 8/1996 | Huebner | |
| 5,601,551 A | 2/1997 | Taylor et al. | |
| 5,620,442 A | 4/1997 | Bailey et al. | |
| 5,624,440 A | 4/1997 | Huebner | |
| 5,628,819 A | 5/1997 | Mestemaker et al. | |
| 5,658,283 A | 8/1997 | Huebner | |
| 5,662,649 A | 9/1997 | Huebner | |
| 5,674,221 A | 10/1997 | Hein et al. | |
| 5,683,389 A | 11/1997 | Orsak | |
| 5,690,633 A | 11/1997 | Taylor et al. | |
| 5,695,496 A | 12/1997 | Orsak et al. | |
| 5,709,681 A | 1/1998 | Pennig | |
| 5,752,954 A * | 5/1998 | Mata | A61B 17/645 606/53 |
| 5,897,555 A | 4/1999 | Clyburn et al. | |
| 5,976,133 A | 11/1999 | Kraus et al. | |
| 6,010,501 A | 1/2000 | Raskin et al. | |
| 6,022,348 A * | 2/2000 | Spitzer | A61B 17/6466 606/324 |
| 6,080,153 A | 6/2000 | Mata et al. | |
| 6,152,925 A | 11/2000 | Marsh et al. | |
| 6,162,223 A | 12/2000 | Orsak et al. | |
| 6,162,224 A | 12/2000 | Huebner | |
| 6,171,309 B1 | 1/2001 | Huebner | |
| 6,176,860 B1 | 1/2001 | Howard | |
| 6,277,119 B1 * | 8/2001 | Walulik | A61B 17/645 606/56 |
| 6,340,361 B1 | 1/2002 | Kraus et al. | |
| 6,342,054 B1 | 1/2002 | Mata | |
| 6,409,729 B1 * | 6/2002 | Martinelli | A61B 17/6466 606/59 |
| 6,520,961 B1 | 2/2003 | Marsh | |
| 6,575,972 B1 | 6/2003 | Gordon | |
| 6,652,523 B1 | 11/2003 | Evrard et al. | |
| 7,252,669 B1 | 8/2007 | McIntyre | |
| 7,407,504 B2 | 8/2008 | Dongar et al. | |
| 7,608,074 B2 | 10/2009 | Austin et al. | |
| 7,806,623 B2 | 10/2010 | Thomke et al. | |
| D633,208 S | 2/2011 | Murner | |
| 8,057,473 B2 | 11/2011 | Orsak et al. | |
| 8,206,388 B2 | 6/2012 | Thomke et al. | |
| 8,303,587 B2 | 11/2012 | Lehmann et al. | |
| 8,444,643 B2 | 5/2013 | Thomke et al. | |
| 8,840,653 B2 * | 9/2014 | Thomke | A61B 17/60 24/335 |
| 9,138,260 B2 * | 9/2015 | Miller | A61B 17/6466 |
| 2001/0034520 A1 | 10/2001 | Enayati | |
| 2002/0004659 A1 | 1/2002 | Boudard et al. | |
| 2002/0042613 A1 * | 4/2002 | Mata | A61B 17/62 606/59 |
| 2002/0151892 A1 * | 10/2002 | Walulik | A61B 17/645 606/57 |
| 2002/0165543 A1 * | 11/2002 | Winquist | A61B 17/6466 606/54 |
| 2003/0149429 A1 | 8/2003 | Ferrante et al. | |
| 2003/0149430 A1 | 8/2003 | Ferrante et al. | |
| 2003/0187432 A1 * | 10/2003 | Johnson | A61B 17/6416 606/59 |
| 2003/0191468 A1 * | 10/2003 | Hoffman | A61B 17/6466 606/59 |
| 2004/0097944 A1 | 5/2004 | Koman et al. | |
| 2004/0133199 A1 | 7/2004 | Coati et al. | |
| 2004/0138659 A1 | 7/2004 | Austin et al. | |
| 2005/0113829 A1 | 5/2005 | Walulik et al. | |
| 2005/0245939 A1 * | 11/2005 | Ferrante | A61B 17/6466 606/96 |
| 2006/0039750 A1 * | 2/2006 | Thomke | A61B 17/645 403/385 |
| 2006/0052781 A1 * | 3/2006 | Thomke | A61B 17/6466 606/59 |
| 2006/0229605 A1 | 10/2006 | Olsen | |
| 2006/0235383 A1 | 10/2006 | Hollawell | |
| 2006/0247629 A1 * | 11/2006 | Maughan | A61B 17/6466 606/53 |
| 2007/0038217 A1 | 2/2007 | Brown et al. | |
| 2007/0100338 A1 | 5/2007 | Deffenbaugh et al. | |
| 2007/0123856 A1 | 5/2007 | Deffenbaugh et al. | |
| 2007/0123857 A1 | 5/2007 | Deffenbaugh et al. | |
| 2007/0198012 A1 * | 8/2007 | Thomke | A61B 17/60 606/54 |
| 2007/0233061 A1 | 10/2007 | Lehmann et al. | |
| 2007/0255280 A1 | 11/2007 | Austin et al. | |
| 2008/0221571 A1 | 9/2008 | Daluiski et al. | |
| 2008/0247818 A1 | 10/2008 | Oesch et al. | |
| 2009/0088751 A1 | 4/2009 | Mullaney | |
| 2009/0198234 A1 * | 8/2009 | Knuchel | A61B 17/62 606/57 |
| 2009/0287212 A1 | 11/2009 | Hirata et al. | |
| 2009/0299368 A1 | 12/2009 | Bauer | |
| 2010/0076436 A1 | 3/2010 | Hajianpour | |
| 2010/0298827 A1 * | 11/2010 | Cremer | A61B 17/6466 606/54 |
| 2011/0082458 A1 | 4/2011 | Crozet et al. | |
| 2011/0098706 A1 | 4/2011 | Mullaney | |
| 2011/0098707 A1 | 4/2011 | Mullaney | |
| 2011/0172664 A1 | 7/2011 | Bagnasco et al. | |
| 2011/0172665 A1 * | 7/2011 | Winquist | A61B 17/6466 606/59 |
| 2011/0230882 A1 | 9/2011 | Ben | |
| 2012/0004659 A1 * | 1/2012 | Miller | A61B 17/60 606/54 |
| 2012/0089142 A1 * | 4/2012 | Mullaney | A61B 17/645 606/54 |
| 2012/0095462 A1 | 4/2012 | Miller | |
| 2012/0150180 A1 | 6/2012 | Verma et al. | |
| 2012/0150184 A1 | 6/2012 | Mullaney | |
| 2012/0150185 A1 | 6/2012 | Mullaney | |
| 2012/0150186 A1 | 6/2012 | Hajianpour | |
| 2012/0203225 A1 | 8/2012 | Mingozzi et al. | |
| 2012/0209266 A1 | 8/2012 | Ottoboni et al. | |
| 2012/0283736 A1 | 11/2012 | Hollawell | |
| 2012/0289959 A1 | 11/2012 | Miller | |
| 2012/0296335 A1 | 11/2012 | Mullaney | |
| 2013/0006244 A1 | 1/2013 | Lehmann et al. | |
| 2014/0214033 A1 * | 7/2014 | Miller | A61B 17/6466 606/59 |
| 2014/0257288 A1 * | 9/2014 | Chang | A61B 17/6466 606/59 |
| 2014/0324045 A1 * | 10/2014 | Cremer | A61B 17/6466 606/54 |
| 2014/0336649 A1 * | 11/2014 | Dorawa | A61B 17/6466 606/59 |

(56) References Cited

U.S. PATENT DOCUMENTS

2014/0350615 A1    11/2014  Holovacs et al.
2014/0364853 A1*   12/2014  Mullaney ............. A61B 17/645
                                                        606/59
2015/0320446 A1*   11/2015  Cremer .............. A61B 17/6466
                                                        606/59

FOREIGN PATENT DOCUMENTS

| EP | 0 469 966 A1 | 2/1992 | | |
|---|---|---|---|---|
| EP | 1016381 A1 * | 7/2000 | ......... | A61B 17/6466 |
| EP | 1016381 A1 | 7/2000 | | |
| EP | 1254640 A2 | 11/2002 | | |
| FR | 2831792 A1 | 5/2003 | | |
| GB | 2033758 A | 5/1980 | | |
| SU | 1281260 A1 | 1/1987 | | |

OTHER PUBLICATIONS

Biomet, DFS Mini Fixator, undated.
Burny et al., The External Minifixator, Orthopaedic and Trauma Service, University Clinic of Brussels, 1983.
Original Hoffmann, Mini-Legthening & External Fixation Device, Howmedica, undated.
The Mini Hoffmann External Fixation System, Howmedica International, undated.
RX-Flx Surgical Technique, OrthoPro, undated.
Vilex Rail Fixation System, Vilex, undated.
Mini Rail System, Surgical Technique, SBI, Small Bone Innovations, Inc., 2010.
EX FI RE, External Fixation Reduction, Osteo AG, undated.
European Search Report for Application No. EP 14154576 dated Jun. 12, 2014.

* cited by examiner

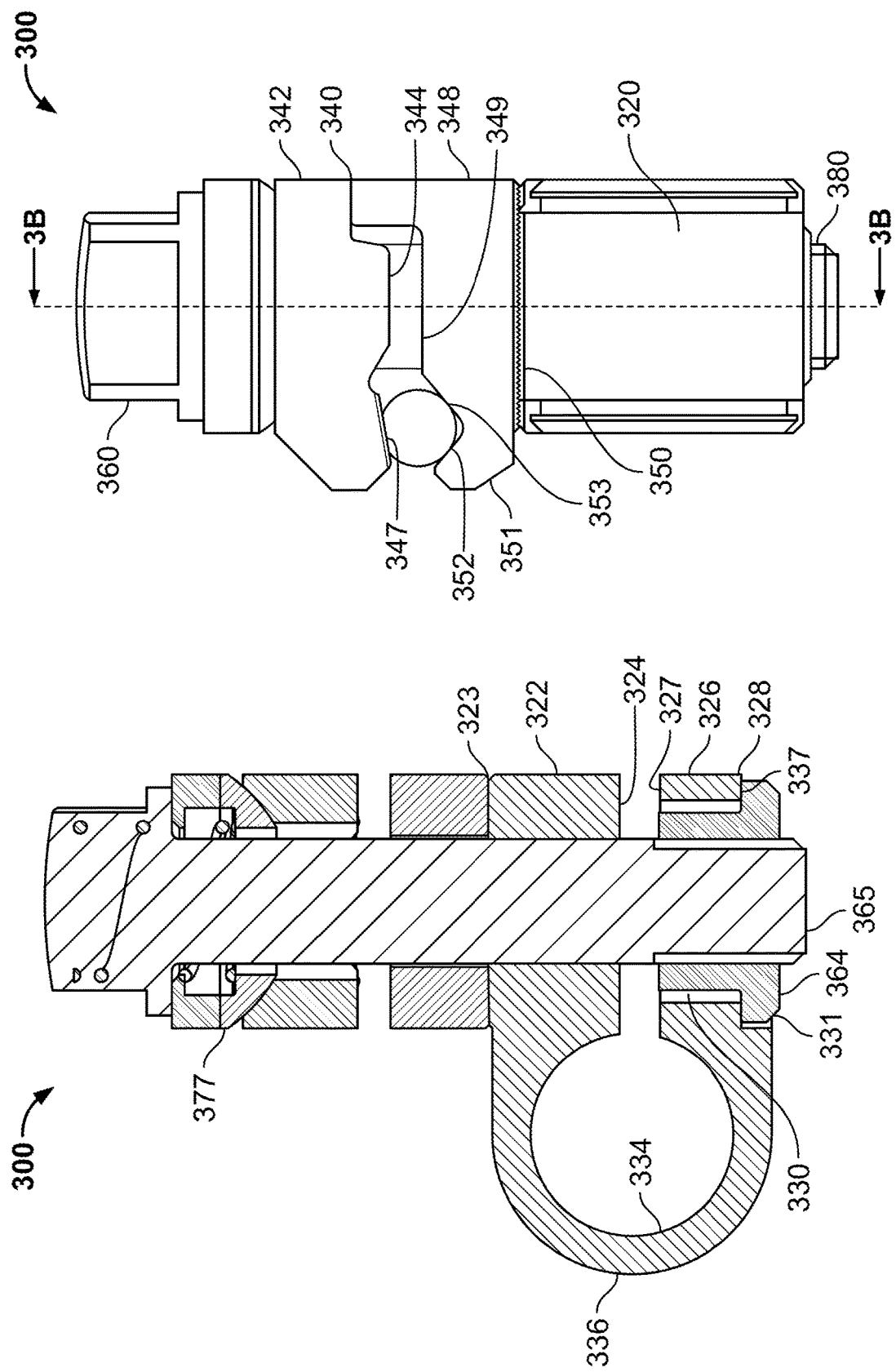

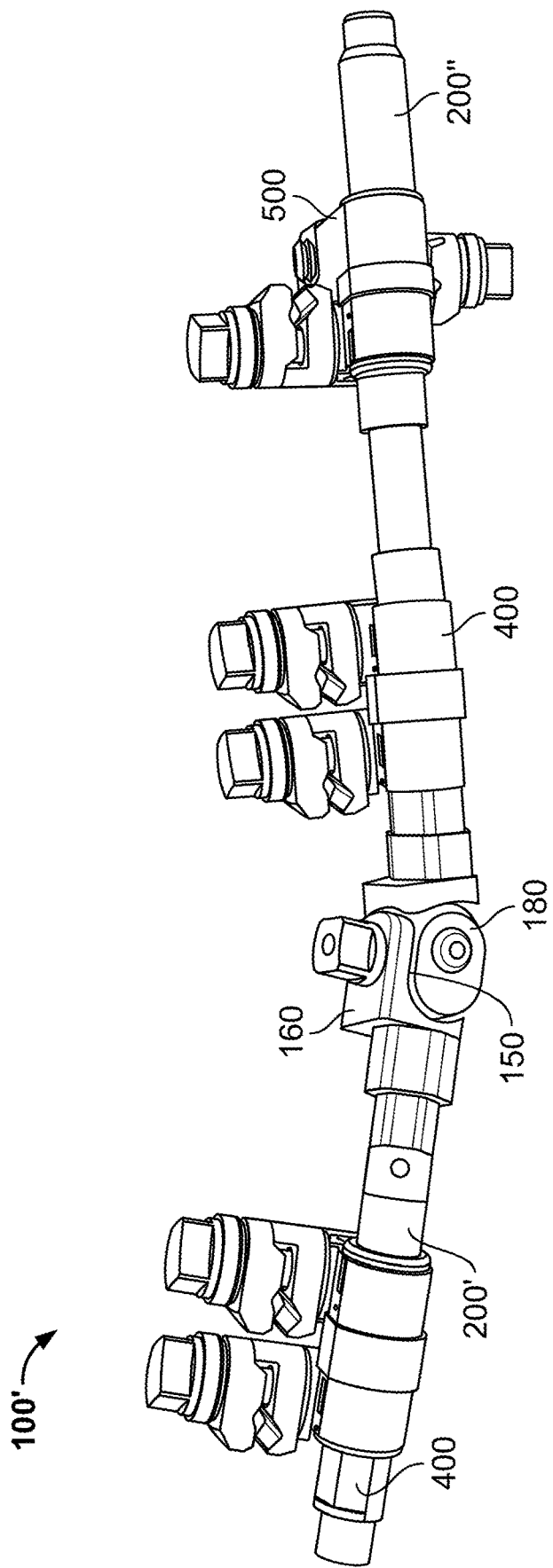

DISTRACTION TUBE WITH WIRE CLAMP

CROSS-REFERENCE TO RELATED APPLICATIONS

This application claims the benefit of the filing date of U.S. Provisional Application No. 62/203,174 filed Aug. 10, 2015, the disclosure of which is hereby incorporated by reference herein.

FIELD OF THE INVENTION

The present invention relates to external fixation systems and methods, and in particular relates to improved fixation pin positioning and orientation using dynamic housing members with clamping portions coupled to a telescoping body.

BACKGROUND OF THE INVENTION

Many different types of bone deformities can be corrected using external fixation systems. Such systems generally use rings, fixation plates, threaded rods or struts for manipulation, angulation, and translation of the deformities of bones.

Some existing fixation systems on the market have components that are static and do not allow for certain adjustment and/or pivoting. Lack of flexibility in a system may restrict attachment to certain bone areas at certain angles as well as restrict motion of the portion of the body that the external fixation system is being attached to in order to correct. Because of such lack of flexibility, such systems may make it more difficult for the physician to achieve an optimal clinical outcome.

Mini-rails are external fixation systems known in the art that are used to control distraction and compression during lengthening or deformity correction procedures generally of small bones. The primary use of these systems are in the hand, foot and craniomaxillofacial ("CMF") regions. Existing mini-rail systems are generally bulky, unnecessarily complex in procedure, and utilize pin configurations that generally flex during correction of bone fragments.

Further, prior art mini-rails generally consist of exposed threaded rods or "cages" which pin clamps translate on. In other prior art systems, the pin clamps may allow for some polyaxial rotation of the pins that are coupled thereto; however, other degrees of freedom are generally restricted between the pin clamps and the fixation rod that the pin clamp is coupled to. Further, many systems are not configured such that other fixation devices could attach to it unless such other fixation devices are specifically designed to interface with the threaded rod or cage thereof, for example.

There exists a need for a dynamic mini-rail system that is not bulky and allows surgeons to insert fixation pins, of different diameters, in multiple bone locations and at a wide variety of angles such that ideal bone may be targeted for the best pin purchase.

SUMMARY OF THE INVENTION

The present invention improves upon existing mini-rails by allowing for greater flexibility in fixation pin clamping and placement. The systems and methods described herein are indicated for use in osteotomies, arthrodeses, lengthening cases, fracture fixations, bone reconstruction procedures, revision procedures, non-unions, and delayed unions.

The systems of the present invention allow a physician to target the best bone possible for ideal pin placement and thread purchase by allowing insertion of fixation pins with different diameters, in multiple bone locations and at a wide variety of angles. The flexibility of the systems of the present invention provide physicians and surgeons the capacity to place pins in the positions they feel are most appropriate. Pairs of fixation pins can be oriented vertically, horizontally, or diagonally with respect to each other. Additionally, the incidence angle of each fixation pin as it is inserted into the bone can be adjusted independently.

The systems described herein also provide cross platform compatibility by way of a standard 8 mm diameter compression/distraction tube that can easily be coupled to other external fixation devices if desired. Further, the mini-rails of the present invention have a built-in thread such that the mini-rails may be used in other external fixation constructs, such as circular and conventional ex-fix systems, for example.

The mini-rail systems described herein utilizes a central telescoping tube that can be locked to at a variety of lengths. Housing members including clamping portions are then slid over the tube. The location of each housing member along the tube may be determined independently of each other.

Each clamping portion can hold two fixation pins of either the same or different diameters (ranging from 2-4 millimeters) through the use of two spring loaded jaws. These two fixation pins can rotate fully and independently about the telescoping tube when the housing members and clamping portions are in an unlocked position. In addition, the spring loaded jaws allow the pin to rotate parallel to the telescoping tube. This bi-axial rotation allows the surgeon to position the pins vertically, horizontally, or diagonally with respect to each other. Tightening of one nut anchors both the pin to the clamping portion and the housing member to the central tube simultaneously.

A first aspect of the present invention is an external fixation device comprising an external fixation system comprising a first elongate rod, a first housing member and a first locking pin. The first housing member has a fixation pin clamping portion and a rod receiving portion, the fixation pin clamping portion having opposing jaws for receiving and clamping a fixation pin, the rod receiving portion including a longitudinal cavity housing at least a portion of the first elongate rod. The first locking pin is coupled to the fixation pin clamping portion and the rod receiving portion of the first housing member, wherein movement of the first locking pin in a first direction causes the opposing jaws of the fixation pin clamping portion and the rod receiving portion to compress toward one another such that the first housing member is in a locked state and cannot move with respect to the first elongate rod.

In accordance with one embodiment of the first aspect of the present invention, the first locking pin is at least partially housed within a longitudinal bore defined by both of the fixation pin clamping portion and the rod receiving portion.

In another embodiment of the first aspect, the longitudinal bore has an axis perpendicular to an axis of the longitudinal cavity of the rod receiving portion.

In yet another embodiment of the first aspect, the a longitudinal axis is defined between the opposing jaws of the fixation pin clamping portion, the longitudinal axis being perpendicular to the longitudinal bore.

In still yet another embodiment of the first aspect, the fixation pin clamping portion and the rod receiving portion are rotatably coupled to one another about the axis of the longitudinal bore. Movement of the first locking pin in the first direction causes the fixation pin clamping portion and the rod receiving portion to compress toward one another such that the fixation pin clamping portion and the rod receiving portion cannot move with respect to one another.

In still yet another embodiment of the first aspect, movement of the first locking pin in a second direction allows the opposing jaws of the fixation pin clamping portion and the rod receiving portion to move away from one another such that the first housing member is in an unlocked state and can move with respect to the first elongate rod.

In still yet another embodiment of the first aspect, the first locking pin includes an actuator portion and a shaft portion, the shaft portion being located within the longitudinal bore, the actuator portion being rotatable in the first direction.

In still yet another embodiment of the first aspect, the rod receiving portion includes first and second deflectable legs, the first and second deflectable legs moving toward one another when the first locking pin is moved in the first direction.

In still yet another embodiment of the first aspect, a second elongate rod has a longitudinal axis coaxial with a longitudinal axis of the first elongate rod when the first and second elongate rods are coupled, and wherein the first and second elongate rods translate with respect to one another along the longitudinal axes thereof.

In accordance with a second aspect of the present invention, an external fixation device comprises a first elongate rod having a longitudinal axis, a first fixation pin portion having opposing jaws for receiving and clamping a fixation pin, a rod receiving portion rotatably coupled to the first fixation pin clamping portion, the rod receiving portion including a longitudinal cavity housing at least a portion of the first elongate rod, and a first locking pin coupled to the fixation pin clamping portion and the rod receiving portion of the first housing member, wherein movement of the first locking pin in a first direction causes the opposing jaws of the fixation pin clamping portion and the rod receiving portion to compress toward one another such that the first housing member is in a locked state and cannot move with respect to the first elongate rod.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 3B is a front assembled view the housing member of FIG. 3A.

FIG. 3C is a cross-section view of the housing member of FIG. 3B taken along line B-B.

FIG. 6 is a perspective view of another embodiment of an external fixation system of the present invention.

DETAILED DESCRIPTION

Figure 1:
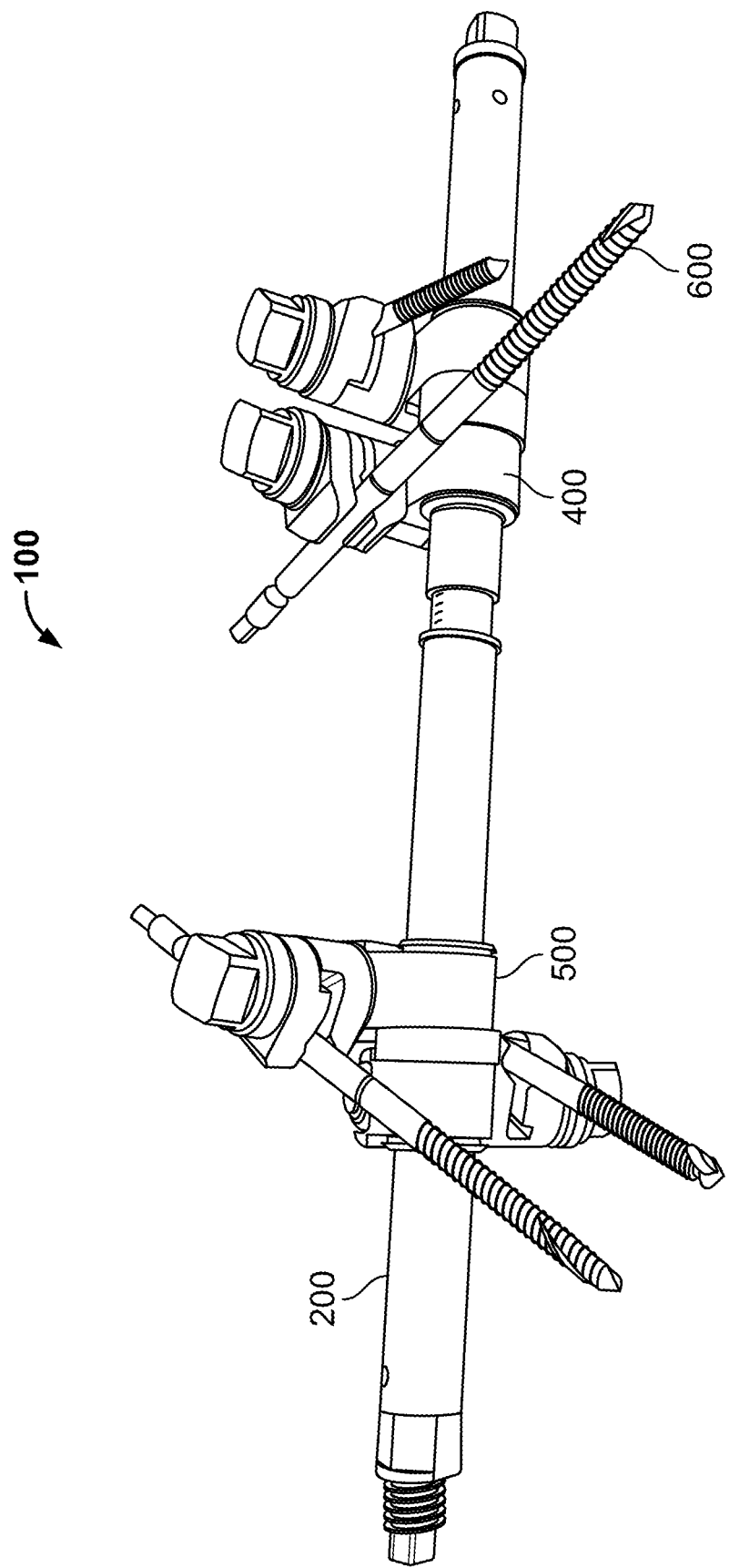
FIG. 1 is a perspective view of one embodiment of an external fixation system of the present invention.

In FIG. 1 there is shown an embodiment of an external fixation system 100 having a distraction tube or telescoping rod 200, a first housing member 400, a second housing member 500, and a plurality of fixation pins 600 coupled to respective clamping portions of the first and second housing members 400, 500.

Figure 2A:
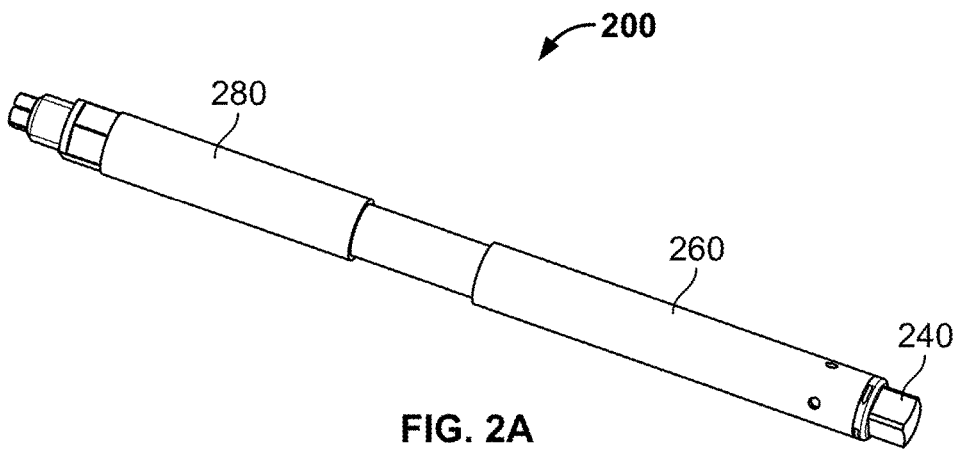
FIG. 2A is a perspective view of a distraction tube of the external fixation system of FIG. 1.
Figure 2B:
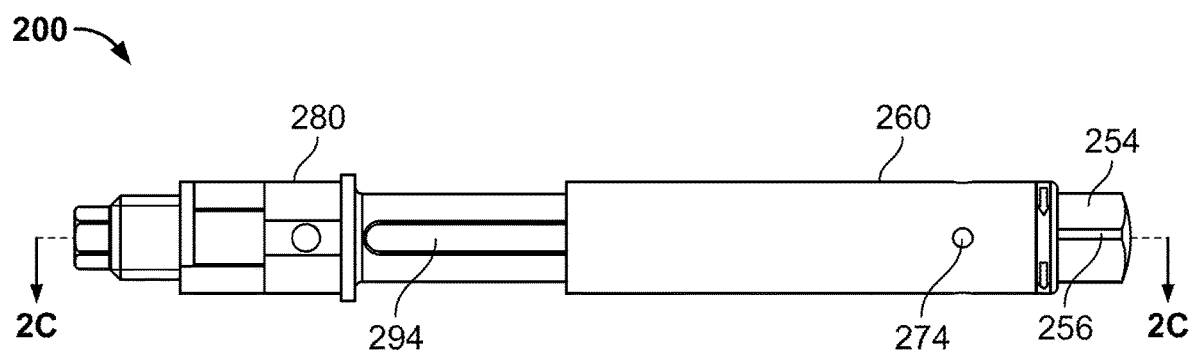
FIG. 2B is a side view of the distraction tube of FIG. 2A.

FIGS. 2A-2B are assembled views of distraction tube 200 having an actuation member 240, a first elongate tube member 260, a second elongate tube member 280, a spring clip 294, a detent 296 and a ball 298.

Figure 2C:
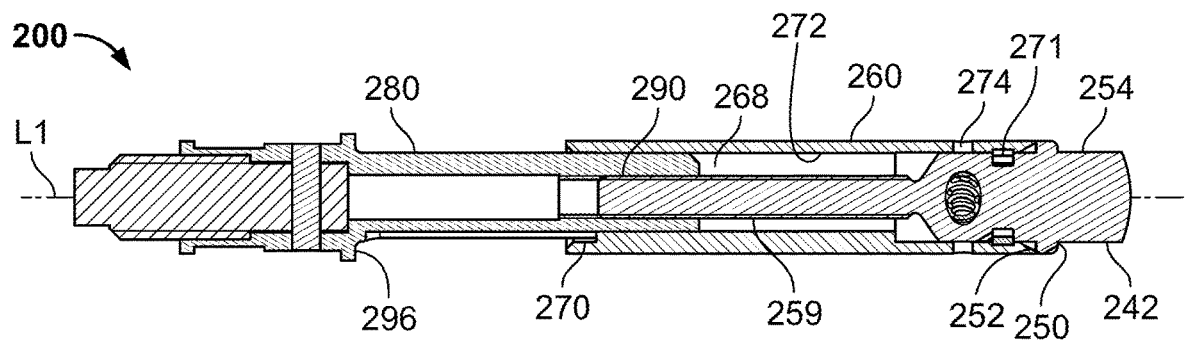
FIG. 2C is a cross-section view of the distraction tube of FIG. 2A taken along line A-A.
Figure 2D:
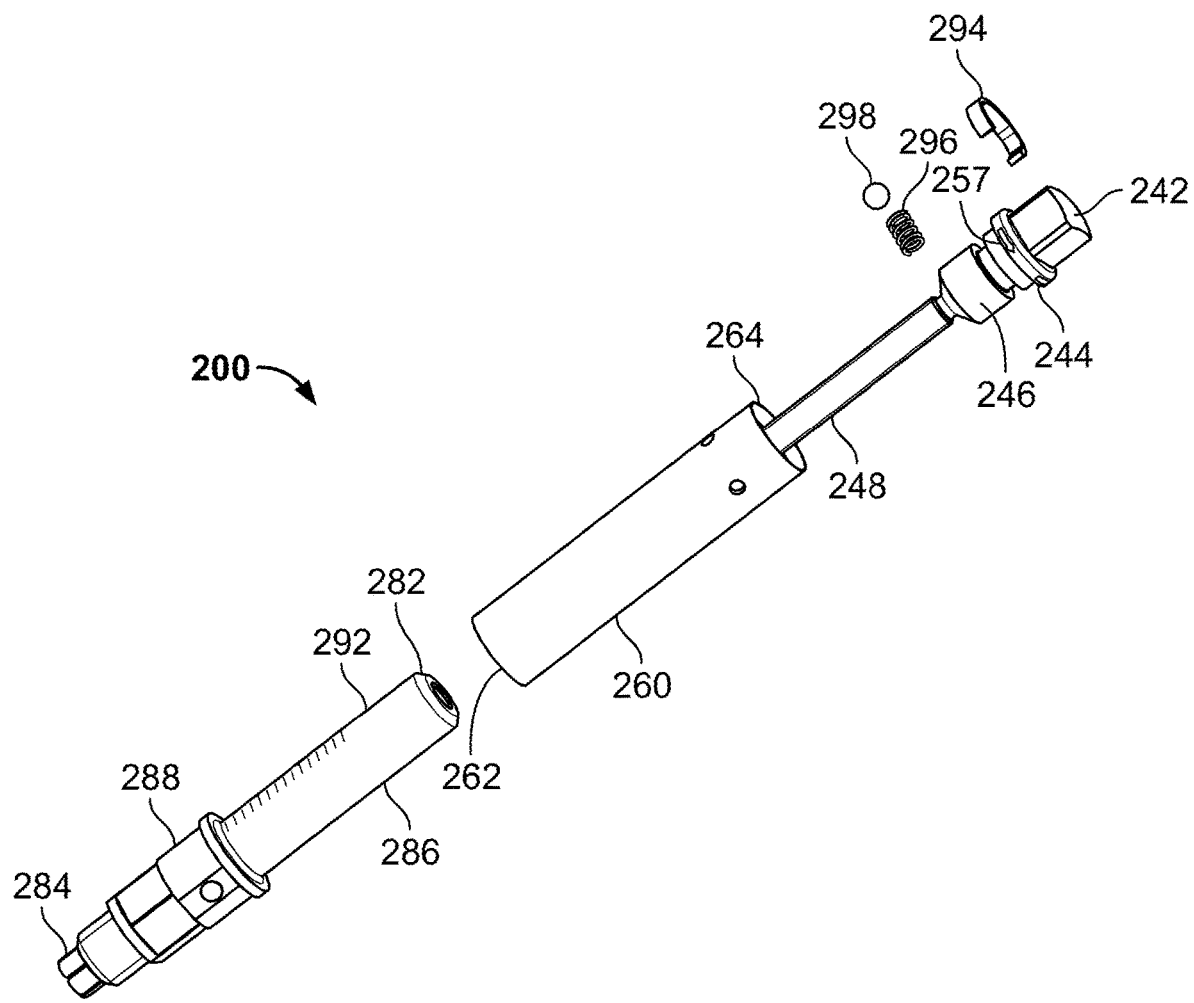
FIG. 2D is an exploded perspective view of the distraction tube of FIG. 2A.

As shown in FIGS. 2C-2D, actuation member 240 includes an actuation portion 242, a base portion 244, an engagement portion 246 and a shaft portion 248. Actuation portion 242 projects outwardly in a distal direction from a distal end surface 250 of base portion 244. Engagement portion 246 projects outwardly in a proximal direction from a proximal end surface 252 of base portion 244. Engagement portion houses at least a portion of detent 296 and ball 298. Shaft portion 248 projects outwardly in a proximal direction from engagement portion 246. Actuation portion 242 is preferably configured to be engaged and manipulated by hand or with a tool. In the embodiment shown, actuation portion 242 has four angled flat surfaces 254 in a square configuration with four rounded edges 256 between adjacent surfaces 254. Engagement portion 246 preferably includes a circumferential recess 257. Shaft portion 248 includes threads 259 along substantially the entire length thereof.

First elongate tube member 260 includes a distal end surface 262 and a proximal end surface 264. First elongate tube member has a bore 268 extending through the proximal and distal end surfaces 262, 264 thereof and a protrusion 270 projecting outwardly from an inner surface 272 thereof. A plurality of apertures 274 are located through a circumference of tube member 260.

Second elongate tube member 280 includes a distal end surface 282, a proximal end portion 284, a tube portion 286 and a shaft portion 288. Tube portion 286 includes an inner threaded surface 290 and an outer surface 292 having a longitudinal recess 294. Proximal end portion 284 is shaped in order to couple second elongate tube member to other external fixation constructs, if desired.

In assembling distraction tube 200, distal end surface 262 of first elongate tube member 260 preferably mates with proximal end surface 252 of base portion 244 of actuation member 240 with shaft portion 248 of actuation member 240 being housed within bore 268 of first elongate member. Spring clip 294 is at least partially received within circumferential recess 257 of actuation member 240 and a corresponding recess 271 within an inner surface 272 of first elongate tube member 260. Rotation of actuation member 240 may be calculated by the interaction of detent 296, ball 298, and the plurality of apertures 274 in first elongate tube member 260. Each 90 degree rotation of actuation member 240 either clockwise or counterclockwise amounts to a 1 mm change in length, for example, of distraction tube 200.

When actuation member 240 is operatively coupled to first elongate tube member 260, engagement portion 246 of actuation member 240 engages inner surface 272 of first elongate tube member 260. Once actuation member 240 and first elongate tube member 260 are coupled, protrusion 270 of first elongate tube member 260 is coupled to longitudinal recess 294 of tube portion 286 at distal end surface 282 of tube portion 286 and slid along longitudinal recess 294 until threaded portion 259 of shaft portion 248 of actuation member 240 comes in contact with inner threaded surface 290 of tube portion 286 of second elongate tube member 280. Actuation portion 242 is then rotated in a clockwise direction in order to thread shaft portion 248 onto threaded surface 290. As actuation portion 242 continues to be rotated in a clockwise direction, protrusion 270 continues to ride along longitudinal recess 294 of tube portion 286 in a first direction until proximal end surface 264 lies adjacent a distal end surface 296 of shaft portion 288. Because protrusion 270 rides along longitudinal recess 294, first elongate tube member 260 does not rotate with respect to second elongate tube member 280. Instead, first elongate tube member 260 only translates with respect to second elongate tube 280 along longitudinal axis L1.

If actuation portion 242 is rotated in a counterclockwise direction, protrusion 270 will continue to ride along longitudinal recess 294 of tube portion 286, but in a second direction along longitudinal axis L1 such that proximal end surface 264 will be separated from distal end surface 296 of shaft portion 288 a larger linear distance from one another. As long as actuation member 240, first elongate tube member 260, and second elongate tube member 280 are coupled to one another, rotation of actuation member 240 in either a clockwise or counterclockwise direction will cause proximal end surface 264 and distal end surface 296 to move closer and further away from one another in a linear direction along longitudinal axis L1 of external fixation system 100.

In another embodiment, tube portion 286 of second elongate tube member 280 has an outer surface 292 that is square shaped and has no longitudinal recess 292 in the outer surface thereof. Also, first elongate tube member 260 has a bore 268 having an inner surface 272 that is square shaped and no protrusion 270 projecting outwardly from the inner surface thereof. In this embodiment, once actuation member 240 and first elongate tube member 260 are coupled, square shaped inner surface 272 of first elongate tube member 260 is coupled to square shaped outer surface 292 of tube portion 286 of the second elongate tube member 280 at distal end surface 282 of tube portion 286 and is slid along the outer surface 292 until threaded portion 259 of shaft portion 248 of actuation member 240 comes in contact with inner threaded surface 290 of tube portion 286 of second elongate tube member 280. Actuation portion 242 is then rotated in a clockwise direction in order to threaded shaft portion 248 onto threaded surface 290.

Figure 3A:
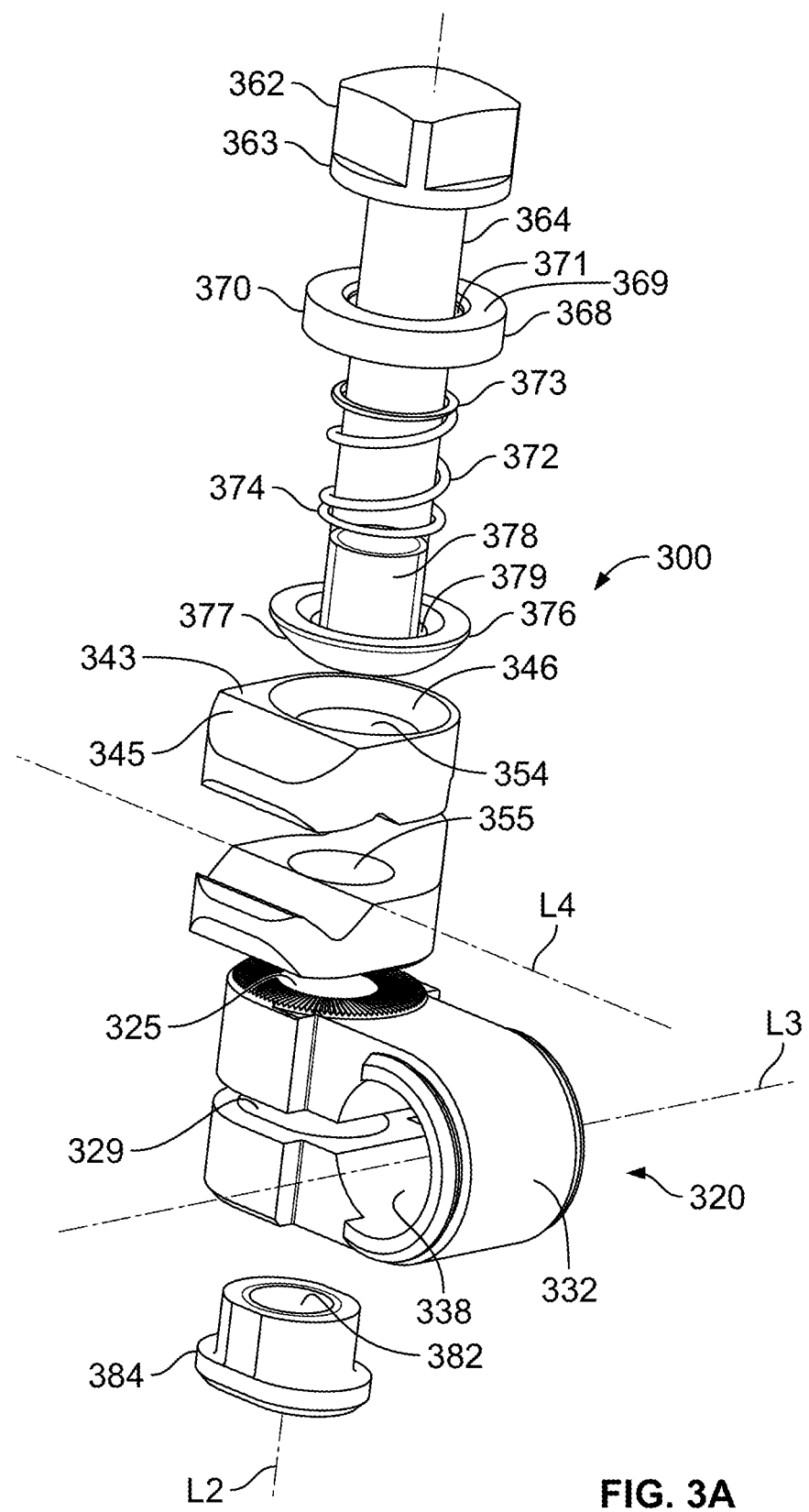
FIG. 3A is an exploded perspective view of an embodiment of a housing member of the present invention.

FIGS. 3A-3C show a first embodiment of a housing member 300 of an external fixation system. Housing member 300 includes a housing portion 320, a clamping portion 340, an actuation portion 360, and a stopper portion 380.

Housing portion 320 includes top and bottom portions 322, 326 coupled by way of a curved connector portion 332. Top and bottom portion 322, 326 may be referred to as deflectable legs for their ability to move toward and away from one another through their connection with curved connection portion 332. Top portion 322 includes a circumferentially grooved superior surface 323, a substantially planar inferior surface 324 and an aperture 325 extending through surfaces 323, 324. Bottom portion 326 includes substantially planar superior and inferior surfaces 327, 328 and a stepped aperture 329 extending through surfaces 327, 328. Stepped aperture 329 has a first aperture portion 330 and a second aperture portion 331. A longitudinal axis L2 extends through surfaces 323, 324, 327, 328 of top and bottom portions 322, 326. Curved connector portion 332 has an inner curved surface 334 and an outer curved surface 336. The coupling of curved connection portion 332 to top and bottom bore portions 322, 326 defines an aperture 338 having a longitudinal axis L3.

Clamping portion 340 includes first and second jaw portions 342, 348. First jaw portion 342 has a superior surface 343, an irregularly shaped inferior surface 344 and an aperture 354 extending through surfaces 343, 344. A chamfer surface 345 and a curved recess surface 346 both extend from superior surface 343 toward inferior surface 344. Inferior surface 344 includes a substantially planar fixation pin contact surface 347. Second jaw portion 348 has an irregularly shaped superior surface 349, a circumferentially grooved inferior surface 350 and an aperture 355 extending through surfaces 349, 350. A chamfer surface 351 extends from inferior surface 350 toward superior surface 349. Superior surface includes angled first and second fixation pin contact surfaces 352, 353.

Actuation portion 360 includes a head portion 362, a shaft portion 364, a first washer 368, a spring 372, and a second washer 376. Head portion 362 and shaft portion 364 may collectively be referred to as a locking pin. Head portion 362 is configured to be rotated manually or with a tool or driver. Head portion 362 terminates at a planar surface 363. First washer 368 has superior and inferior surfaces 369, 370 and an aperture 371 extending through superior and inferior surfaces 369, 370. Spring 372 has a superior end 373 and an inferior end 374. Second washer 376 has a spherical head portion 377, a shaft portion 378 and an aperture 379 extending through the spherical head portion 377 and shaft portion 378.

Housing member 300 is first assembled by lining up actuation portion 360, clamping portion 340, housing portion 320 and stopper portion 380 along longitudinal axis L2. In doing so, apertures 354, 355 of first and second jaw portions 342, 348 of clamping portion 340 and apertures 325, 329 of top and bottom portions 322, 326 of housing portion 320 are aligned along longitudinal axis L2. First washer 368, then spring 372, then second washer 376 are assembled onto shaft portion 364 of actuation portion 360 such that shaft portion 364 extends through apertures in first washer 368, spring 372 and second washer 376. Shaft portion 364 is then inserted through the aligned apertures 354, 355 of first and second jaw portions 342, 348 of clamping portion 340 and apertures 325, 329 of top and bottom portions 322, 326 of housing portion 320 until a distal end 365 of shaft portion 364 is at least partially located within stepped aperture 329 of bottom portion 326 of housing member 320. Stopper portion 380 is then at least partially inserted into aperture 329 and coupled to distal end 365 of shaft portion 364. This coupling may be a compression fit, but is preferably a threaded connection. Threads located on an inner surface 382 of stopper portion 380 engage threads on an outer surface 366 of shaft portion 364.

Once the components of housing member 300 are generally assembled as described above, housing member 300 can now be assembled to an elongated rod or distraction tube 200, for example, of an external fixation system 100 of the present invention. This assembly occurs by inserting an end of an elongate rod or distraction tube 200, for example, through aperture 338 of housing member 300 such that longitudinal axis L1 of distraction tube 200 is substantially coaxial with longitudinal axis L3 of aperture 338. In order to insert distraction tube 200 into and at least partially through aperture 338, housing member 300 should be in an unlocked state such that the inferior surface 324 of top portion 322 and superior surface 328 of bottom portion 326 are not in contact with one another and are separated from one another by a substantially planar distance. In this unlocked state, aperture 338 has a neutral or relaxed diameter. Once the housing member 300 is located at a desired position about the length of the distraction tube 200, actuation portion can be actuated in order to bring the inferior surface 324 of top portion 322 and superior surface 328 of bottom portion 326 into contact with one another while compressing the diameter of aperture 338 such that the position and orientation of housing member 300 with respect to distraction tube 200 is set. In this locked state, a linear distance between the head portion 362 of actuation portion 360 and stopper portion 380 is less than a linear distance between the head portion 362 of actuation portion 360 and stopper portion in the unlocked state.

In an unlocked state, housing member 300 may rotate about longitudinal axis L1. Further, first and second jaw portions 342, 348 of clamping portion 340 may rotate with respect to top portion 322 of housing portion 320 about longitudinal axis L2 which is preferably perpendicular and offset to longitudinal axis L1. Jaw portions 342, 348 generally correspondingly rotate about longitudinal axis L2 because of irregularly shaped inferior surface 344 of jaw portion 342 having a corresponding shape to superior surface 349 of jaw portion 348. Further still, in the unlocked state, jaw portions 342, 348 may be distracted away from or compressed toward longitudinal axis L4 such that the space between surfaces 347 of jaw portion 342 and surfaces 352, 353 of jaw portion 348 may be made greater or less depending on the location of the jaw portions 342, 348.

In clamping a fixation pin 600 such as that shown in FIG. 1 and FIG. 3B, for example, fixation pin 600 is inserted into the space between surfaces 347 of jaw portion 342 and surfaces 352, 353 of jaw portion 348 at a particular position about the length of fixation pin 600. As head portion 362 of actuation portion 360 begins to rotate in a clockwise manner about longitudinal axis L2, the components of housing member 300 begin to compress toward one another. A user should set the position and orientation of housing member 300 with respect to distraction tube 200. The jaw portions 342, 348 should be rotationally aligned with respect to housing portion 320 in a desired position by engaging the grooves of the circumferentially grooved superior surface 323 with the grooves of the circumferentially grooved inferior surface 350. As head portion 362 of actuation portion 360 continues to rotate in a clockwise manner, the stopper portion 380 is brought into full engagement within stepped aperture 329 such that a contact portion 384 of stopper portion 380 comes into contact with a ledge portion 337 located at a base of aperture 331 of bottom portion 326 of housing portion 320. Further rotation of head portion 362 of actuation portion 360 causes the position of fixation pin 600 to be fixed with respect to surfaces 347 of jaw portion 342 and surfaces 352, 353 of jaw portion 348. The housing member is now in a fully locked state such that the location and orientation of fixation pin 600 and housing member 300 with respect to distraction tube 200 is set.

Figure 4A:
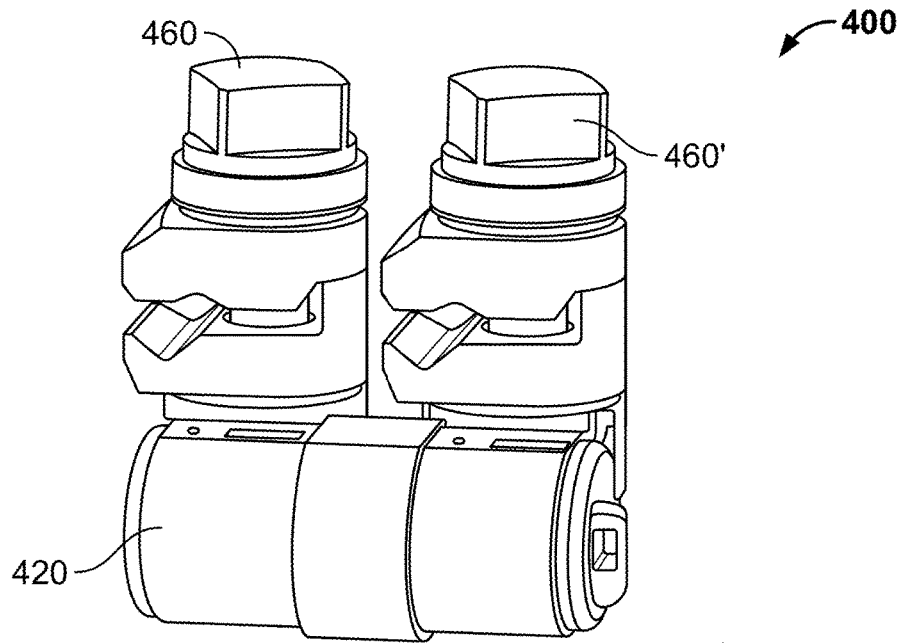
FIG. 4A is a perspective view of another embodiment of a housing member of the external fixation system of FIG. 1.
Figures 4B, 4C:
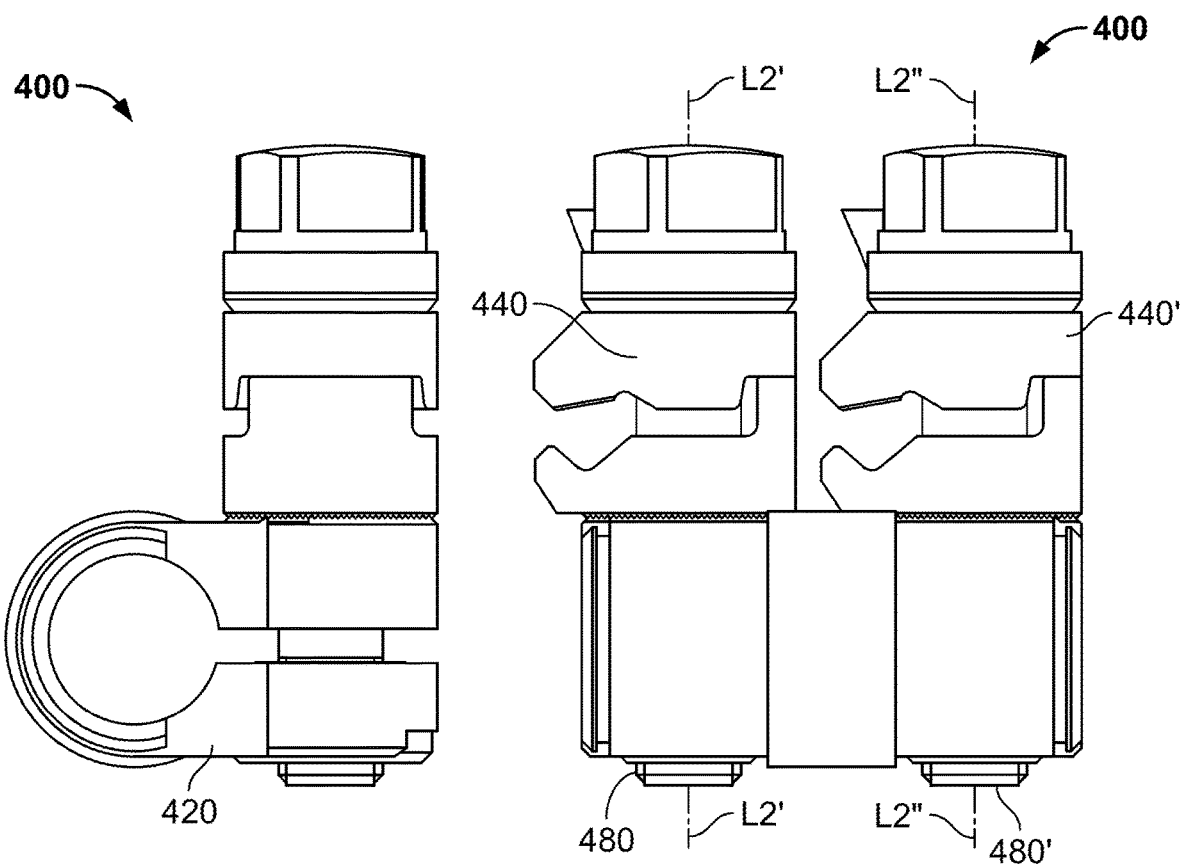
FIG. 4B is a side view of the housing member of FIG. 4A.
FIG. 4C is a front view of the housing member of FIG. 4A.

FIGS. 4A-4C show an embodiment of a housing member 400 of external fixation system 100 shown in FIG. 1. The difference between housing member 300 and housing member 400 is that housing member 400 includes an additional clamping portion, actuation portion and stopper portion. I should be understood that the components of housing member 400 and their interaction with each other is the same as was described with respect to housing member 300, with like reference numerals referring to like features in the present embodiment. Specifically, housing member 400 includes a housing portion 420, a first clamping portion 440, a second clamping portion 440', a first actuation portion 460, a second actuation portion 460', a first stopper portion 480 and a second stopper portion 480'. This embodiment provides a physician, surgeon or any other operating room personnel with additional fixation pin coupling such that a first fixation pin can be coupled to first clamping portion 440 while a second fixation pin can be coupled to second clamping portion 440'. Because first and second clamping portions 440, 440' are able to be oriented and locked independently of one another, different size fixation pins and different locations and orientations of the fixation pins can be produced using housing member 400. As shown in FIG. 1, for example, housing member 400 allows pin 600 to have a first pin trajectory located in a first clamping portion and another pin to have a second pin trajectory located in a second clamping portion. Each pin shown has a different diameter, wherein pin 600 may be 4 mm in diameter while the second pin may be 2 mm in diameter, for example. Further, housing portion 420, first clamping portion 440, first actuation portion 460, and first stopper portion 480 define a longitudinal axis L2' while housing portion 420, second clamping portion 440', second actuation portion 460' and second stopper portion 480' define a longitudinal axis L2''. Longitudinal axes L2' and L2'' are generally parallel and offset to one another.

Figure 5A:
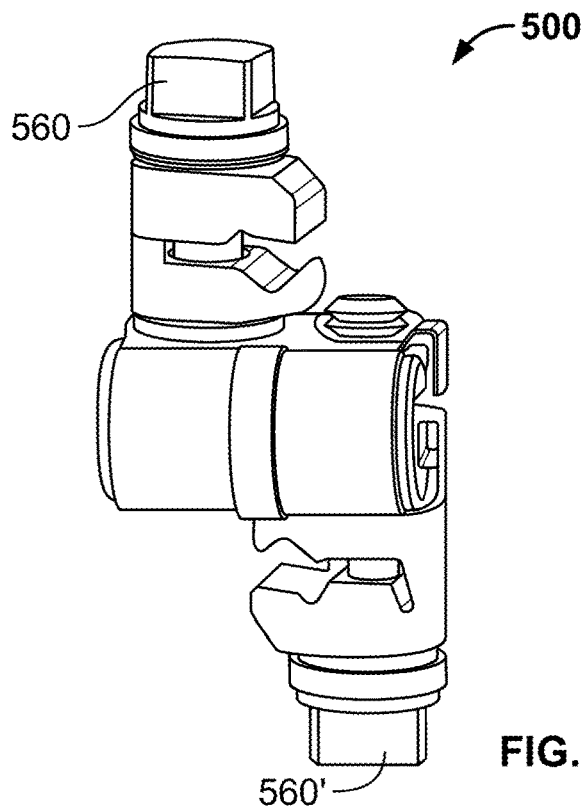
FIG. 5A is a perspective view of another embodiment of a housing member of the external fixation system of FIG. 1.
Figure 5B:
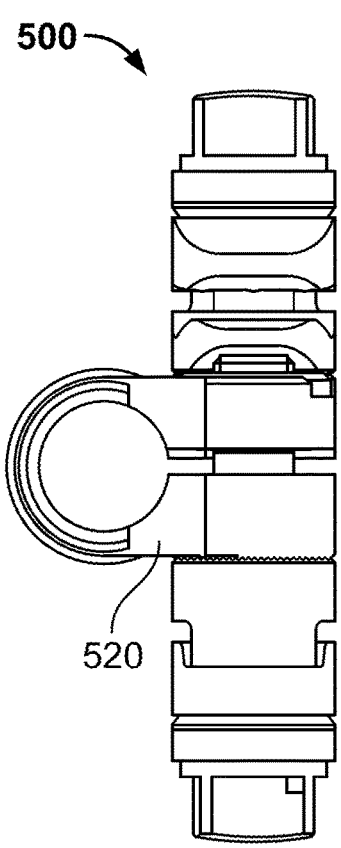
FIG. 5B is a side view of the housing member of FIG. 5A.
Figure 5C:
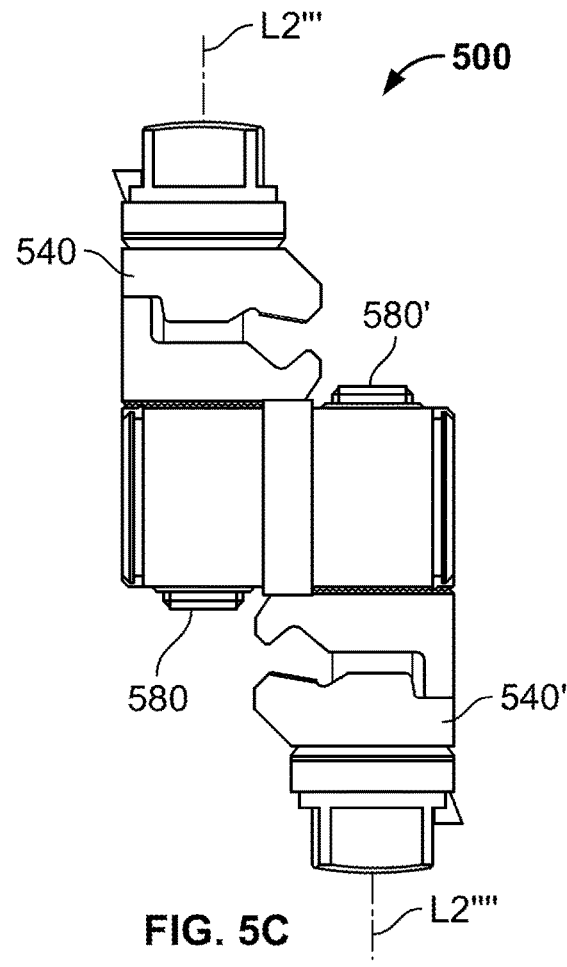
FIG. 5C is a front view of the housing member of FIG. 5A.

FIGS. 5A-5C show another embodiment of a housing member 500 of external fixation system 100 shown in FIG. 1. The difference between housing member 500 and housing member 400 is that housing member 500 includes first and second groups of clamping portions, actuation portions and stopper portions located in opposite directions of one another. It should be understood that the components of housing member 500 and their interaction with each other is the same as was described with respect to housing member 300, with like reference numerals referring to like features in the present embodiment. Specifically, housing member 500 includes a housing portion 520, a first clamping portion 540, a second clamping portion 540', a first actuation portion 560, a second actuation portion 560', a first stopper portion 580 and a second stopper portion 580'. This embodiment provides a physician, surgeon or any other operating room personnel with variability in set fixation pins about longitudinal axis L1 of external fixation system 100. As with housing member 400, because first and second clamping portions 540, 540' are able to be oriented and locked independently of one another, different size fixation pins and different locations and orientations of the fixation pins can be produced suing housing member 500. Housing portion 520, first clamping portion 540, first actuation portion 560, and first stopper portion 580 define a longitudinal axis L2''' while housing portion 520, second clamping portion 540', second actuation portion 560' and second stopper portion 580' define a longitudinal axis L2'''' such that longitudinal axes L2''' and L2'''' are generally parallel and offset to one another.

Another embodiment of an external fixation system 100' is shown in FIG. 6. External fixation system 100' includes a first distraction tube 200', a second distraction tube 200'', first and second housing members 400 and a housing member 500. Additional flexibility with respect to orienting fixation pins is provided with external fixation system 100' by way of joint 150. Distraction tube 200' terminates at a first joint end 160 while distraction tube 200" terminates at a second joint end 180. First joint end interacts with second joint end 180 such that distraction tube 200' can pivot with respect to distraction tube 200" in several directions. Such a construct may be advantageous for use with articulating bones and/or joints.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An external fixation system comprising:
a first elongate rod;
a first housing member having a fixation pin clamping portion, a rod receiving portion, and only a single helical spring, the fixation pin clamping portion having a first jaw and a second jaw opposing the first jaw for receiving and clamping a fixation pin between the first and second opposing jaws, the rod receiving portion coupled to the second jaw and including a first leg, a second leg connected to the first leg by a coupling portion and a longitudinal cavity housing at least a portion of the first elongate rod, the second leg having a stepped recess;
a first locking pin having a head and a shaft having a thread, the first locking pin coupled to the fixation pin clamping portion and the rod receiving portion of the first housing member;
a stopper having a thread engaged to the thread of the shaft,
wherein the single helical spring is positioned adjacent the head of the first locking pin and between a portion of the head and a portion of the first jaw, and wherein movement of the first locking pin in a first direction causes the opposing jaws of the fixation pin clamping portion to compress toward one another, the first leg and the second leg of the rod receiving portion to compress such that the first housing member is in a locked state and cannot move with respect to the first elongate rod and the stopper to move within the stepped recess and into engagement with a step of the stepped recess such that the thread of the stopper is positioned inside the second leg of the rod receiving portion.

2. The external fixation system of claim 1, wherein the first locking pin is at least partially housed within a longitudinal bore defined by both of the fixation pin clamping portion and the rod receiving portion.

3. The external fixation system of claim 2, wherein the longitudinal bore has an axis perpendicular to an axis of the longitudinal cavity of the rod receiving portion.

4. The external fixation system of claim 3, wherein a longitudinal axis is defined between the opposing jaws of the fixation pin clamping portion, the longitudinal axis being perpendicular to the longitudinal bore.

5. The external fixation system of claim 3, wherein the fixation pin clamping portion and the rod receiving portion are rotatably coupled to one another about the axis of the longitudinal bore.

6. The external fixation system of claim 5, wherein movement of the first locking pin in the first direction causes the fixation pin clamping portion and the rod receiving portion to compress toward one another such that the fixation pin clamping portion and the rod receiving portion cannot move with respect to one another.

7. The external fixation system of claim 1, wherein movement of the first locking pin in a second direction allows the opposing jaws of the fixation pin clamping portion and the rod receiving portion to move away from one another such that the first housing member is in an unlocked state and can move with respect to the first elongate rod.

8. The external fixation system of claim 1, wherein the head of the first locking pin is an actuator and rotatable in the first direction.

9. The external fixation system of claim 1, wherein the rod receiving portion includes first and second deflectable legs, the first and second deflectable legs moving toward one another when the first locking pin is moved in the first direction.

10. The external fixation system of claim 1, further comprising a second elongate rod having a longitudinal axis coaxial with a longitudinal axis of the first elongate rod when the first and second elongate rods are coupled, and wherein the first and second elongate rods translate with respect to one another along the longitudinal axes thereof.

11. An external fixation system comprising:
a first elongate rod having a longitudinal axis;
a first fixation pin clamping portion having a first jaw and a second jaw opposing the first jaw for receiving and clamping a fixation pin;
a rod receiving portion rotatably coupled to the second jaw, the rod receiving portion including a first leg, a second leg connected to the first leg by a coupling portion and a longitudinal cavity housing at least a portion of the first elongate rod, the second leg having a stepped recess;
a first locking pin including a head and a shaft having a thread, the first locking pin at least partially disposed within a longitudinal bore defined by both the fixation pin clamping portion and the rod receiving portion;
a spring positioned adjacent the head of the first locking pin and between a portion of the head and a portion of the first jaw; and
a stopper having a thread for engaging the thread of the shaft,
wherein movement of the first locking pin in a first direction causes the opposing jaws of the fixation pin clamping portion to compress toward one another, the first leg and the second leg of the rod receiving portion to compress such that the first housing member is in a locked state and cannot move with respect to the first elongate rod and the stopper to move within the stepped recess and into engagement with a step of the stepped recess such that the thread of the stopper is disposed within the longitudinal bore.

12. The external fixation system of claim 11, wherein the longitudinal bore has an axis perpendicular to an axis of the longitudinal cavity of the rod receiving portion.

13. The external fixation system of claim 12, wherein a longitudinal axis is defined between the opposing jaws of the fixation pin clamping portion, the longitudinal axis being perpendicular to the longitudinal bore.

14. The external fixation system of claim 12, wherein the fixation pin clamping portion and the rod receiving portion are rotatably coupled to one another about the axis of the longitudinal bore.

15. The external fixation system of claim 14, wherein movement of the first locking pin in the first direction causes the fixation pin clamping portion and the rod receiving portion to compress toward one another such that the fixation pin clamping portion and the rod receiving portion cannot move with respect to one another.

16. The external fixation system of claim 11, wherein movement of the first locking pin in a second direction allows the opposing jaws of the fixation pin clamping portion and the rod receiving portion to move away from one another such that the first housing member is in an unlocked state and can move with respect to the first elongate rod.

17. The external fixation system of claim 11, wherein the head of the first locking pin is an actuator and rotatable in the first direction.

18. The external fixation system of claim 11, wherein the rod receiving portion includes first and second deflectable legs, the first and second deflectable legs moving toward one another when the first locking pin is moved in the first direction.

19. The external fixation system of claim 11, further comprising a second elongate rod having a longitudinal axis coaxial with the longitudinal axis of the first elongate rod when the first and second elongate rods are coupled, and wherein the first and second elongate rods translate with respect to one another along the longitudinal axes thereof.

* * * * *